United States Patent [19]

Bens et al.

[11] 4,400,819

[45] Aug. 23, 1983

[54] DEVICE FOR THE ACCURATE ANATOMICAL LOCATING OF TOMODENSITOMETRIC SECTIONS

[75] Inventors: Jean Bens; Marcel Bloch; Réne Chekroun; Remy Klausz, all of Paris, France

[73] Assignee: Compagnie Generale de Radiologie, Paris, France

[21] Appl. No.: 142,474

[22] Filed: Apr. 21, 1980

[30] Foreign Application Priority Data

Apr. 23, 1979 [FR] France ............................... 79 10211

[51] Int. Cl.³ ............................................. G01N 23/02
[52] U.S. Cl. ..................................... 378/20; 378/163; 33/174 D
[58] Field of Search .................. 250/312, 445 T, 476, 250/491; 33/1 N, 174 D, 474

[56] References Cited

U.S. PATENT DOCUMENTS

| 3,307,262 | 3/1967 | Chaiken | 250/476 |
| 3,714,428 | 1/1973 | Gasaway | 250/445 T |
| 3,952,194 | 4/1976 | Bayonnet | 250/476 |
| 4,144,460 | 3/1979 | Norman | 250/451 |
| 4,174,481 | 11/1979 | Liebetruth | 250/445 T |
| 4,319,136 | 3/1982 | Jinkens | 250/476 |

FOREIGN PATENT DOCUMENTS 955637  4/1964  United Kingdom ............ 33/174 D

*Primary Examiner*—Alfred E. Smith
*Assistant Examiner*—Carolyn E. Fields
*Attorney, Agent, or Firm*—Oblon, Fisher, Spivak, McClelland & Maier

[57] ABSTRACT

Means for locating accurately without ambiguity tomodensitometric sections sloping in any way with respect to an original predetermined plane. At least one locating element is disposed on the part to be examined by conventional tomodensitometry, this element having a baseline situated in the original plane and having at least one characteristic such as density, varying continuously or substantially continuously along a direction perpendicular to this baseline, the variation of this characteristic being measurable on the tomodensitometric images of the different sections; this characteristic may be in particular a dimension of the element: width perpendicular to the direction perpendicular to the base in the case where the element is a triangle.

19 Claims, 16 Drawing Figures

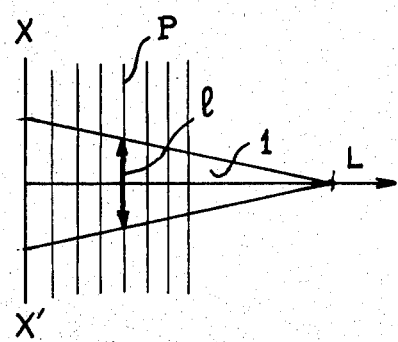
FIG_1
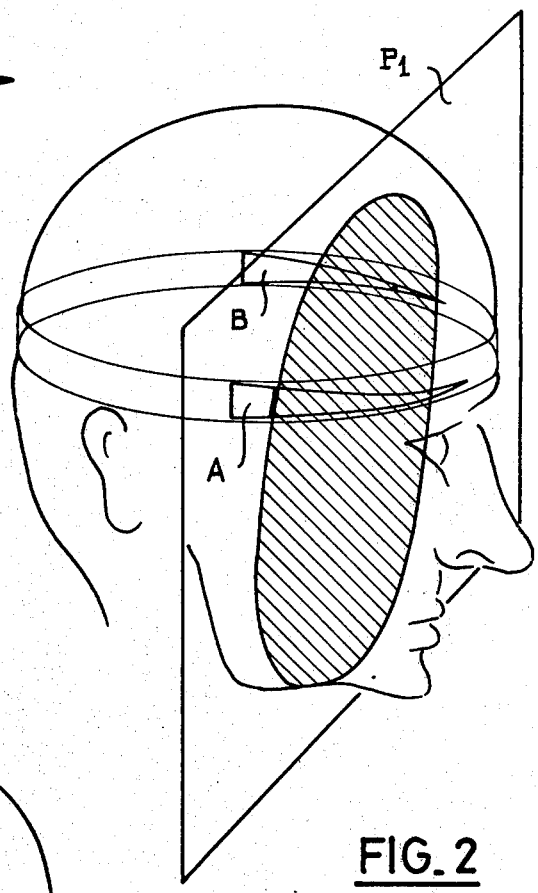
FIG_2
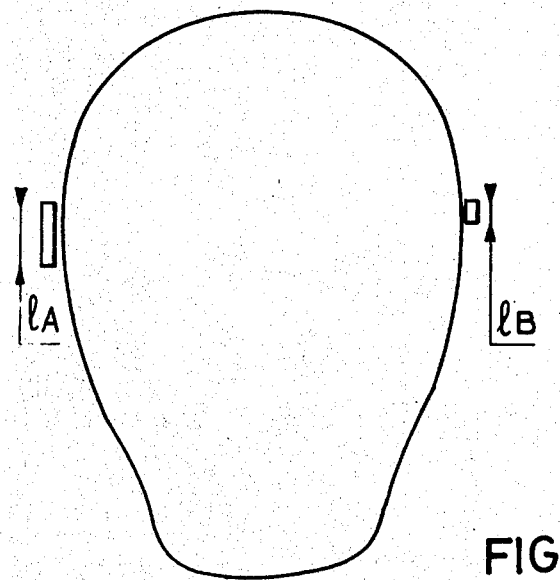
FIG_3

DEVICE FOR THE ACCURATE ANATOMICAL LOCATING OF TOMODENSITOMETRIC SECTIONS

BACKGROUND OF THE INVENTION

1. Field of the Invention

The present invention relates to a device for locating easily and with great accuracy tomodensitometric sections made on a subject to be examined, this location being made in relation to conventional and predetermined anatomic planes of a subject.

2. Description of the Prior Art

Tomodensitometry apparatus are now well-known and will not be described here. It is sufficient for understanding the subject matter of the present invention to know that, whatever the type of tomodensitometry contemplated, it enables images to be obtained of the different slices of the patient examined. These slices of examination, called tomodensitometric sections, are generally perpendicular to the longitudinal axis (or great axis) of the subject to be examined. They may however be sloping with respect to this axis. This is particularly the case when it is a matter of producing tomodensitometric sections of the head. In this case the sections may be parallel to the orbito-meatal plane, i.e. in a plane slightly inclined with respect to the plane normal to the longitudinal axis of the patient; they may also be parallel to the frontal plane of the subject, i.e. perpendicular to the above-described sections.

It may be further useful in some cases to have sections inclined with respect to the different planes which have just been defined.

It is conventional to equip tomodensitometers with locating devices which enable the operator to recognize the sections which he is making, not only in relation to each other, but in relation to the anatomy of the patient examined.

There exist at present different types of locating devices; two of these types of devices are briefly recalled here.

U.S. Pat. No. 4,117,337 describes a locating device using light centering which, from previous relatively complex adjustments, enable a plane to be defined on the subject to be examined which will be the reference plane. All the sections subsequently made will be located with respect to this reference plane. Such a system presents, besides its complexity, different drawbacks. On the one hand it requires previous adjustment which is relatively time consuming to achieve. Defining a reference plane which is not tied to the subject to be examined but to the optical centering device requires practically absolute immobility of the patient at the risk of losing all efficiency, and must be redone for each new examination, which is a considerable disadvantage.

Another type of locating device is described in U.S. Pat. No. 4,115,691. This device, much simpler than the preceding one, includes in a small cylinder which is placed against the subject to be examined. This small cylinder includes different juxtaposed portions along the different sections to be effected. Each portion includes a number which will be visualized in the tomodensitometric image and which enables the different sections to be identified in relation to each other. This device, though it is much simpler than the preceding one, presents however certain drawbacks. It is in fact indispensable for the sections to be perpendicular to the cylinder containing the locating numbers. Furthermore, the first section must be suitably positioned with respect to this cylinder, so as not to be astride two adjacent portions, which would make the reading of the two numbers impossible. Such a device requires then previous adjustment of the first section with respect to the length of the small cylinder. Moreover, it does not enable sections to be made at any angle of incidence.

SUMMARY OF THE INVENTION

The present invention provides a device for easily locating the different sections in relation to the anatomy of the subject to be examined, requiring no previous adjustment of the positioning of the sections, and enabling sections to be conveniently located having different slopes with respect to any reference plane.

According to the invention, a device for the accurate anatomical location of the tomodensitometric sections effected on a subject by means of a tomodensitometer includes at least one elongated element, disposed on the subject in a reproducible way, this element being formed, at least partly, from a material visible on the tomodensitometric sections, and having at least one characteristic whose magnitude varies along its large dimension (direction L), always in the same direction and continuously or substantially continuously, this element being visualized on the tomodensitometric images of the sections to be located by means of a trace on which the measurement of the variable magnitude is carried out so as to obtain the location of the sections along L.

An important advantage of the device of the invention is, besides its great simplicity, that it can be used whatever the position of the sections along direction L, this being possible because the characteristic which provides the location varies continuously along L.

DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 1 shows one embodiment of an element of the locating device in accordance with the invention.

FIG. 2 shows one application of the locating device of the invention including two elements such as that of FIG. 1.

FIG. 3 shows schematically a tomodensitometric section made with a locating device in accordance with that shown in FIG. 2.

DETAILED DESCRIPTION OF THE PREFERRED EMBODIMENTS

Figure 4A:
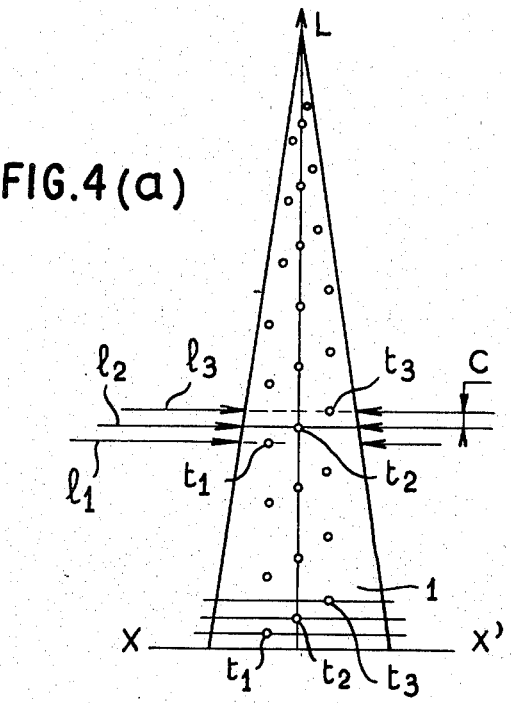
FIGS. 4(a) and 4(b) show another embodiment of the element of FIG. 1.

The device for locating tomodensitometric sections in accordance with the invention enables, as was mentioned above, sections to be located in relation to each other and in relation to the anatomy of the subject, practically whatever the orientation of these sections. Such a possibility is particularly advantageous when examining the head of the subject, which may require not only transverse sections, i.e. perpendicular to the longitudinal axis of the subject, but also non-transverse sections, for example parallel to this axis or even sloping with respect to this axis. It should however be noted that, although the description which follows is more particularly made for examinations of the head, the locating device of the invention may also be used when it is a matter of carrying out examinations of other parts of the body than the head. All that is then required is to dispose this locating device at the place where it is desired to carry out examinations.

FIG. 1 shows schematically a triangular element 1, used by the locating device of the invention. The description of this element and its method of use will enable the basic principle of the invention to be understood, this principle giving a great freedom in use of the device.

A locating device in accordance with the invention includes at least one element such as triangle 1 disposed on the subject to be examined. This triangle 1 is here an isosceles triangle made from a material chosen with a density between 1 and 1.2 for example, so as to appear clearly in the tomodensitometric image of the sections, without introduction of any artifact.

The element formed by triangle 1 has, along direction L, a characteristic whose magnitude varies continuously depending on the position along L. This characteristic is the triangle width 1 intersected by straight lines parallel to axis XX'. Axis XX' merging here with the base of triangle 1, forms a reference axis. The reference axis may be any straight line parallel to the base of the triangle and distinct from this base; reference axis XX' will be called hereafter "baseline"; the angle of the triangle, formed by the two sides intersecting along direction L will be called "angle at the apex".

If tomodensitometric sections of this triangle are made parallel to axis XX', its trace on the tomodensitometric image is a small rectangle whose thickness is the thickness of triangle 1 and whose height, called width in the rest of the text, depends on the position of the section along direction L.

The invention includes in disposing on the subject, in the region to be examined, at least one element such as triangle 1, and in measuring on the tomodensitometric image the width of the trace of triangle 1. The knowledge of the width of this trace will indicate without ambiguity, and for each position of the section along L, the exact position of the examination plane in relation to the baseline XX' of triangle 1. It is sufficient to position triangle 1 in a known way, and preferably reproducibly, on the part examined, to have an accurate anatomical location easy to achieve of the tomodensitometric sections effected.

The measurement of the dimension of this fine trace presents no difficulty. In fact, most tomodensitometers existing at present enable an absolute measurement to be made of the distances on the images which they give. If, for a section whose mean plane intersects triangle 1 of FIG. 1 along trace P, a trace is obtained whose dimension is 1, the reciprocal unequivocal correspondence existing between the position of P along L and the width of 1 indicates without ambiguity the position of this plane P. It is possible, so as to facilitate location, to graduate directly triangle 1 by indicating along L a number of widths 1. The measurement of the magnitudes 1 on the tomodensitometric images will indicate directly, through this correspondence, the position of the mean plane of the section made.

In the description which has just been given, where the locating device includes a single element such as triangle 1, location is achieved with respect to an axis, here the reference axis XX'. It is clear that this may be used for tomodensitometric sections having any slope with respect to the great axis of the subject, since it is sufficient to position this triangle 1 so that its base (i.e. axis XX'), is parallel to the planes of the sections which have just been made. It is also clear that there is no need to carry out previous adjustment of the first section with respect to triangle 1. In fact, since the characteristic which enables the position of the plane of section P to be determined along L varies continuously, an accurate measurement may be obtained whatever the position of this sectional plane along L. It may again be noted that this was not possible with discrete indexing systems such as was the case in the above-mentioned U.S. Pat. No. 4,115,691.

It should however be noted that it is generally necessary to locate the tomodensitometric sections not with respect to an axis such as XX', but with respect to a reference plane. The locating device of the invention lends itself very readily to such locations.

FIG. 2 shows schematically a locating device in accordance with the invention for locating a tomodensitometric sectional plane with respect to a predetermined reference plane. In the example shown in this figure, it is a question of making approximately vetical tomodensitometric sections of the head of a patient to be examined. Two elements in the form of a triangle A and B, such as previously described, are disposed on each side of the head of the patient (on the right and on the left), their two parallel baselines defining a reference plane. The two triangular elements A and B are for example formed from a material having a certain flexibility so as to be able to follow approximately the external contours of the head of the subject. They may be fixed to the head by any appropriate means such as self-adhesive tape, elastic or other headband etc . . . If the tomodensitometric sections are made along planes parallel to the reference plane defined by the two baselines of the triangles, the traces of the two triangles A and B on the tomodensitometric views are equal. On the other hand, if the plane of section $P_1$, while remaining parallel to the baselines of both triangles, is no longer parallel to the reference plane, the traces will no longer be equal, as shown in FIG. 3. Widths $1_A$ and $1_B$ of these two traces give an accurate indication of the position and of the slope of the sectional planes such as $P_1$ with respect to the reference plane. The ratio of these two widths is characteristic of the slope of the sectional plane $P_1$ with respect to the reference plane. Their respective magnitude is characteristic of the distance from the sectional plane to the reference plane. The measurement of these two magnitudes indicates then accurately and without any ambiguity the position of each section with respect to the anatomy of the subject.

It is particularly convenient, after having carried out a first set of tomodensitometric sections thus located, to carry out a second one. It is not necessary to carry out again the locating operations. It is also very convenient to pass from a radiological examination of the patient to a surgical operation. It is sufficient either to keep the two triangular elements A and B in position between the two operations or to reposition them exactly in the same way.

It is to be noted that the greater the opening of the angle at the apex of the locating triangles the higher the locating accuracy.

Figure 4B:
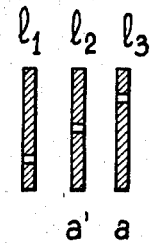

FIGS. 4a and 4b show schematically another embodiment of the triangular elements such as A and B for further increasing the accuracy of the measurement. For this it is sufficient to dispose along the different traces parallel to axis XX' physical marks which will appear distinctly on the traces of the triangle in the tomodensitometric views. These marks are disposed as shown in FIG. 4a for example, i.e. one mark per trace, and are staggered from one trace to the next one by a distance which will appear clearly on the traces of the tomodensitometric views (FIG. 4b). In the example shown here these marks include of small holes made in the triangle; in this same example, where the holes are grouped in threes ($t_1$, $t_2$, $t_3$), three adjacent widths $l_1$, $l_2$, $l_3$, not very different in value, which could have led to confusing them on the tomodensitometric views, are well differentiated by the position in the width of the trace thereof of holes $t_1$, $t_2$ and $t_3$. If c is the distance between two successive holes in the same group, and if d is the diameter of these holes, the maximum error is then: $\pm c/2 - d$.

It is to be noted that it is possible to provide a variation of the locating elements by using, as characteristic varying continuously along direction L, the density of the material forming the locating element. In this case, the element may be formed from a simple elongated strip, rectangular for example, whose length is direction L and whose width, perpendicular to L, defines a "baseline". In this case, it is the density variation which indicates the position of the trace of the sectional plane. This variation has the double advantage of not requiring previous adjustment since a trace may be located wherever it may be along direction L, and of enabling planes inclined by varying angles to be located with respect to the plane defined by the baselines of the two such strips disposed on each side of the subject to be examined.

It is possible, by combining a variation of width l of the locating element and a variation of density to obtain improved accuracy by combining the result of the two measurements. For that, the locating elements are triangular elements as already described and the material which forms them varies continuously, or practically continuously, along the direction L thereof. In this case, the tomodensitometric images contain traces of the triangles whose width depends on the position of the trace of the sectional plane along L, and whose intensity on the visualized image also depends on this position. All that is then required is to combine the information about the dimensions of these traces (as previously indicated), with the information given by the measurement of the radiological density of the traces of the elements on the reconstructed tomodensitometric sections.

Different methods, conventional in themselves, may be used for obtaining the triangle having such a continuous or practically continuous variation of density along direction L. A first method includes in incorporating in the material forming the triangle a powder of a material of different density, the proportion of this powder varying continuously from the base of the triangle to its apex. Another method includes in forming this triangle from several small elementary triangles placed side by side interlockingly (head to tail), so that the base of one is adjacent the apex of the other, these triangles being formed from materials having different densities.

In the examples illustrated in FIGS. 1 and 2, the triangles are isosceles triangles; this form is not indispensable in these variations. They may very well be non-isosceles triangles, rectangles for example or even other elongated geometric forms other than triangles.

In the example of FIG. 2, the sectional planes are approximately parallel to the longitudinal axis of the subject. If it is desired to make sections perpendicular to this axis, i.e. transverse sections, all that is required is to dispose triangles A and B at 90° from the position shown in FIG. 2.

In all the embodiments of the invention which have just been described, though it is possible to locate sectional planes having a certain slope with respect to a reference plane, it is not possible to locate accurately sectional planes sloping in any way whatsoever. In fact, it has been said up to now that it was necessary for the sectional planes to always be parallel to the baseline of the locating elements such as triangles A and B. In fact, if the triangles were no longer intersected along traces parallel to their baselines, the information obtained would be false. Other variations will now be described which enable any angles of incidence to be located with all the accuracy desired.

Figure 5A:
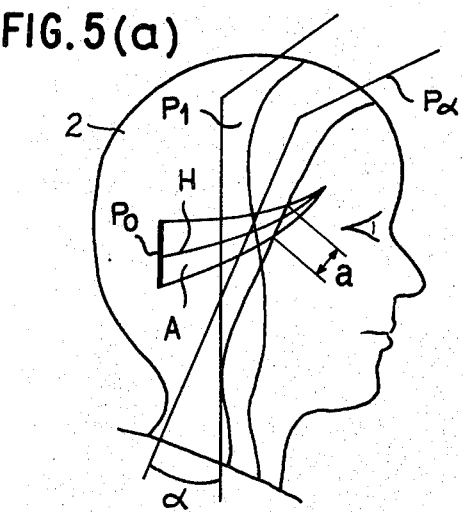
FIGS. 5(a), 5(b) and 5(c) are schematical views of another improved variation of the device of the invention.
Figure 5C:
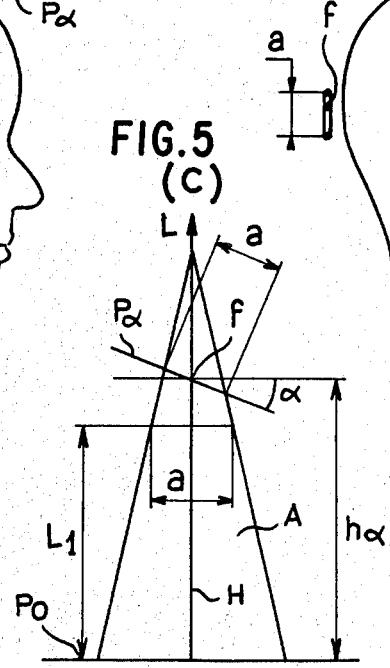
Figure 5B:
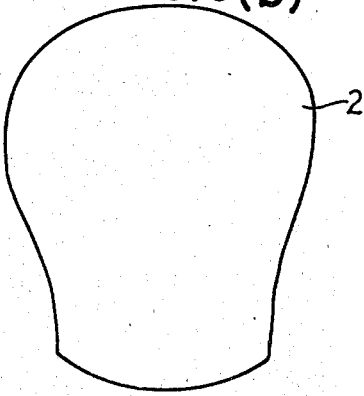

FIGS. 5a, 5b and 5c enable the improvement provided by these variations to be understood.

In FIG. 5a can be seen a triangle A fixed to the head 2 of a patient; the base of this triangle A is approximately parallel to the longitudinal axis of the patient. This base defines, with that of a second identical triangle B, not visible in the figure, but disposed identically on the other side of the patient, an approximately vertical reference plane in this example. This plane $P_0$ will be taken as the original plane on the patient. As long as tomodensitometric sections are made along planes such as $P_1$ parallel to original plane $P_0$, the triangles previously used are sufficient and the trace a (FIG. 5b) of these triangles accurately indicates the position of $P_1$ in relation to $P_0$. On the other hand, when tomodensitometric sections are made which are no longer parallel to the base of triangle A, but which are sloping through an angle $\alpha$ in relation to original plane $P_0$, the measurement of the trace a (FIG. 5b) of the triangle on the tomodensitometric image no longer gives suitable information as to the location of plane $P\alpha$.

FIG. 5c shows how a variation of the locating device of the invention enables suitable and accurate locating of the distance of plane $P\alpha$ with respect to the original plane $P_0$ and of the slope $\alpha$ of this plane $P\alpha$.

If one were satisfied, making the section along plane $P\alpha$, in measuring the width a of the trace of triangle A, one would obtain, as shown in FIG. 5a, a location of this plane $P\alpha$ indicating that it is a sectional plane intersecting triangle A along trace a parallel to its base and spaced from this base by the length $L_1$ (FIG. 5c). The correct measurement should indicate that it is a plane intersecting triangle A along the trace $P\alpha$ shown in FIG. 5c. This trace $P\alpha$ is sloping by an angle $\alpha$ with respect to the base of the triangle, trace a being then between the two sides of the triangle, on $P\alpha$. A suitable location must then give the two pieces of information: angle $\alpha$; height $h\alpha$ with respect to the base of the triangle corresponding to the original plane $P_0$ on the patient. It appears clearly that if the previously described variations are used, locating of the sectional plane with respect to the original plane would be all the more erroneous since sectional plane $P\alpha$ would be sloping with respect to this original plane.

The variations for suitably locating such planes $P\alpha$ include in using one or more triangular-shaped locating elements such as triangle A, capable of giving, besides the dimension of the trace of the triangle on the sectional plane, supplementary information from which slope $\alpha$ may be deduced. This information will be deduced from additional marks situated inside the area of triangle A, these marks being themselves visible in the trace of the triangle on the tomodensitometric image. A particularly suitable mark for obtaining this information about slope $\alpha$, includes materializing the height H of the triangle (merging with the previously described direction L), i.e. the bisectrix of its angle at the apex.

This height H may be for example materialized by a metal wire stuck along height H on triangle A. Since this metal wire has a different density from that of the material forming triangle A, it will appear on trace a of the angle (FIG. 5b) in the form of a dot f of a different brightness from the rest of the trace. Different embodiments of the triangle thus completed will be described hereafter.

When the sectional plane is parallel to the original plane $P_0$, the trace f will be centered at the middle of the trace a of the triangle. When the sectional plane $P\alpha$ is sloping by an angle $\alpha$ with respect to the original plane $P_0$, this trace f will no longer be at the center of trace a. It clearly appears that if the trace of length a is transferred to the triangle of FIG. 5c so that its two edges coincide with the edges of triangle A and so that trace f coincides with height H, one and only one position of trace $P\alpha$ is possible. This position defines the slope and the height $h\alpha$ of the trace of plane $P\alpha$ with respect to the base of triangle $P_0$. These two pieces of information $\alpha$ and $h\alpha$ may be obtained as will be described further on, either by calculation, or by a system of plotters.

One particular embodiment of the locating device thus improved will now be described with the help of FIGS. 6 and 7.

In the example of FIG. 6, where it is a question of making tomodensitometric sections, either approximately vertical, or sloping in relation to the vertical, two triangles A and B will be disposed on each side of the head of the patient to be examined, a single one A of these triangles being visible in the figure. These two triangles are for example formed by two isosceles triangles of known dimensions, made from Plexiglass, on which are stuck metal wires of a diameter sufficiently small so as not to create an artifact on the tomodensitometric sections and sufficiently large for the wires to be perfectly distinguished from the Plexiglass on the image of the densitometric section. These metal wires which may, in one example, be formed by copper wire of a diameter of 0.4 mm, are three in number per triangle and are stuck along the two equal sides of the isosceles triangles and on the bisectrices of the angles at the apex of these triangles. The two lateral wires materialize the edges of triangle A; their distance on the tomodensitometric section indicates the magnitude a of the trace of the triangle. The central wire corresponds to the height H of the triangle; its trace f gives the additional information required for obtaining correct locating not only of the distance but also of the angulation. It is to be noted that the lateral wires may be fixed at a distance from the edges of the Plexiglass support triangle, and even that the support (not visible in the reconstructed images) may have any form; it is in fact the lateral wires which define the edges of the locating element. It is even possible, if the wires are sufficiently rigid, not to have any support; in this case the wires are for example soldered together and maintained, at the rear (base of the triangle) by means of a simple rod.

The two Plexiglass triangles A and B are fixed to adapters 3 which engage in the external auditory apertures of the subject to be examined, these adapters being themselves integral with a part 4 made from Plexiglass for example. Part 4, in the form of a hoop, bears on the nasion of the subject and is secured by means of the two adapters 3 engaged in the ears of the subject. The triangles A and B are positioned about adapters 3 so that the height H of triangles A and B (materialized by the central wire) merges with the orbito-meatal plane of the subject. The base of triangles A and B is then perpendicular to this orbito-meatal plane. The two bases or baselines which may, as already pointed out, be distinct from the bases of the triangles, define an original plane $P_0$ on the patient. On tomodensitometric sections parallel to original plane $P_0$ (sections whose traces are located by means of the parallel straight lines $P_1$ in FIG. 6a), the reconstituted tomodensitometric images will show on each side of the head of the subject three points corresponding to the edges of the triangle and to its height, the central point being equidistant from the external points. The distance between the external points of each trace indicates the distance of the sectional plane $P_1$ with respect to the original plane $P_0$. If these distances are not equal on the two traces situated on each side of the section of the head, it is because the sectional plane is right- or left-sloping as was explained with reference to FIGS. 2 and 3.

Figure 6A:
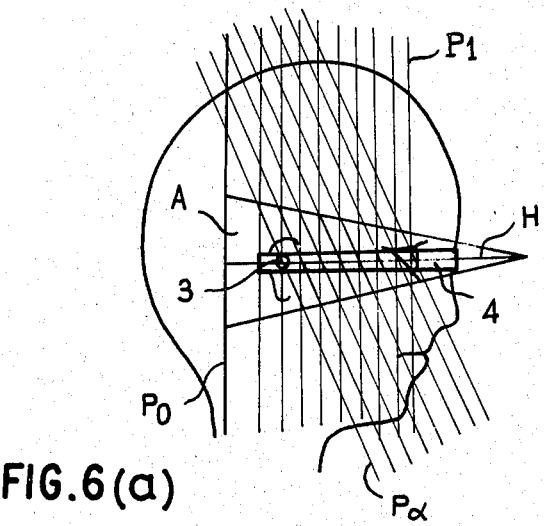
FIGS. 6(a) and 6(b), 7(a) and 7(b) are schematical views of two applications of the variation shown in FIG. 5.
Figure 6B:
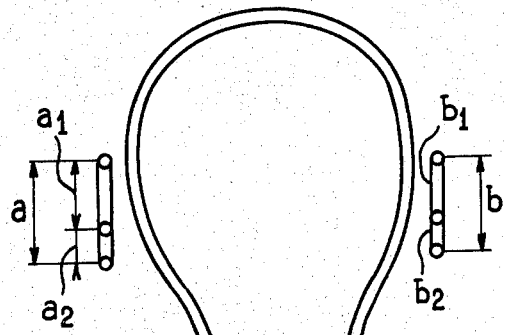

If it is a question of sectional planes $P \alpha$ sloping by an angle $\alpha$ with respect to the original plane $P_0$ (the traces of such planes being located by means of parallel lines $P \alpha$ in FIG. 6a) the tomodensitometric image includes on each side of the head of the subject two traces each including three points, the central point being no longer equidistant from the two external points (FIG. 6b). Here again, if the sectional planes $P \alpha$ are furthermore sloping to the right or left, the two traces are not equal.

Figure 7A:
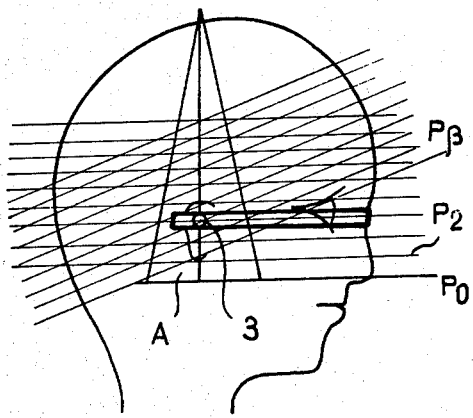

FIGS. 7a and b and illustrate the use of the same device as that which has just been described including two triangles made from plexiglass provided with three wires, mounted on a hoop fixed in the auditory apertures of the subject and on his nasion; but here the two triangles A and B are orientated at 90° from what they were in FIG. 6. This enables tomodensitometric sections parallel to the anatomical reference plane of the subject (parallel traces $P_2$ in FIG. 7a) to be accurately located. This device also enables sectional planes to be located which slope by an angle $\beta$ with respect to the original plane on the subject, which is this time a plane $P_0$ parallel to the previously defined orbito-meatal plane. This original plane $P_0$ may furthermore be merged with the orbito-meatal plane.

In the example which has just been described, the two triangles are plexiglass triangles provided with three metal wires. It is clear that any variation for visualizing on the tomodensitomeric images the edges and the height of the triangle is in accordance with the invention. It is for example possible to use triangles made from a material directly visible on the tomodensitometric images, and to form along their height H a groove which will itself appear on the tomodensitometric images. It is further possible to use a triangle made from a material visible on the tomodensitometric images and to dispose along the height H a wire of a different density, without having wires on the edges of the triangle.

It is to be noted that the device for securing on the subject the two triangles which have just been described (hoop 4 and adapters 3) may also be used for the previously described variations: triangles without wires and rectangles with varying density.

There will now be described with the help of FIG. 8 a method using plotters for rapidly obtaining from the traces of the locating device of the invention visible on the tomodensitometric images, the distance and angulation information of the sectional planes in relation to the original plane.

After having made, calculated and visualized a tomodensitometric section with the conventional means of tomodensitometers, all that is required is to process one after the other the traces a and b of FIG. 6 for example in the following way so as to obtain the precise location of a sectional plane P with respect to the original plane $P_0$ of FIG. 6a.

Figure 8:
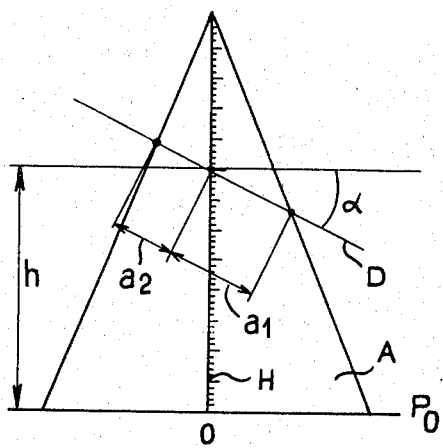
FIGS. 8, 9 and 10 are diagrams showing the plotters used for obtaining the data for locating any sectional planes in relation to a predetermined original plane.
Figure 9:
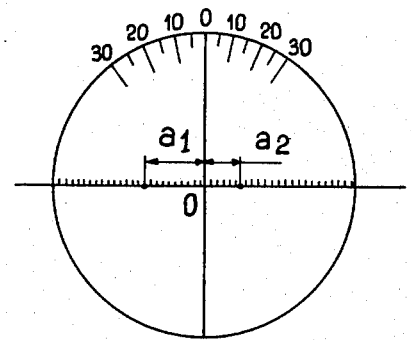
Figure 10:
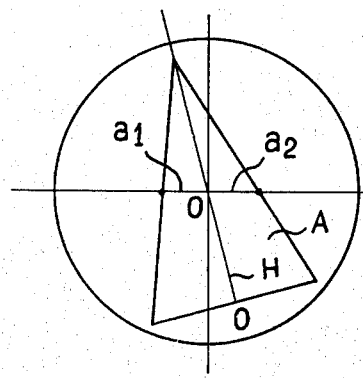

FIGS. 8, 9 and 10 show schematically how it is possible to locate any sectional plane in relation to the original plane with the help of plotters relatively simple in use.

The basic principle of these plotters includes superimposing on a triangle A (FIG. 8) reproducing exactly the triangle A disposed on the patient, a straight line D on which are transferred end to end the two lengths $a_1$ and $a_2$. It is enough to cause the three points representing the ends of lengths $a_1$ and $a_2$ to coincide with the two sides and the height of the isosceles triangle A to obtain at h the height of the section and at $\alpha$ the angle of incidence of this section. This transferring of the straight line D and of the two magnitudes $a_1$ and $a_2$ on the triangle may be easily carried out by using a circular angle protractor illustrated in FIG. 9. The center of the protractor of FIG. 9 corresponds to zero. Lengths $a_1$ and $a_2$ are transferred on each side of this zero, on the diameter marked in millimeters, while locating which correspond respectively to the top and to the bottom of the tomodensitometric section. On this protractor is superimposed (as shown in FIG. 10) the triangle of FIG. 8, which is make from a transparent material such as Plexiglass and whose height H is graduated in millimeters, the base of height H corresponding to the zero point of the original plane $P_0$. This superimposition of the triangle on the protractor is carried out by causing the height H to pass through the center 0 of the protractor; the two sides of the triangle are made to coincide with the ends of the lengths $a_1$ and $a_2$ transferred on the diameter of the protractor. With this superimposition effected, the sectional height is read on the graduated height H of the triangle, at the intersection of this height and the graduated diameter of the protractor; the angulation of the section is read on the protractor, opposite the apex of the isosceles triangle A.

If the two traces a and b of FIG. 6b are identical, it is because the trace of the sectional plane is the same on both triangles and because this plane keeps the bilateral symmetry of the head of the subject examined. It will be then sufficient to carry out this plotting operation once more to obtain the accurate locating of the sectional plane. If on the contrary the two traces are different this operation must be carried out twice on the two pieces of information a and b so as to obtain the position of the sectional plane, whose trace is different on both triangles A and B.

Figure 7B:
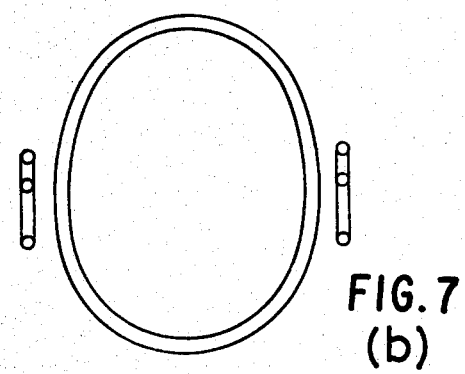

The operation is the same when it is a question of locating the planes P $\beta$ of FIG. 7. The only difference is that the slope is no longer top to bottom, but front to back.

Figure 11:
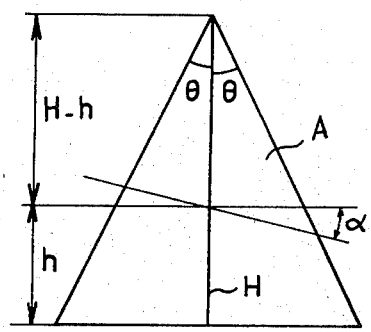
FIG. 11 is a diagram explaining one method for calculating the data for locating any sectional planes in relation to a predetermined original plane.

This method of determining parameters for locating the sectional plane by means of plotters is not extremely accurate, since three points must be superimposed on three straight lines by trial and error. It is possible to obtain much greater accuracy by calculation from measurements $a_1$ and $a_2$ (and possibly $b_1$ and $b_2$ when they are different). If $\theta$ is the half-angle at the apex of the isosceles triangle (FIG. 11), the sectional height h with respect to the original plane (base of the triangle) and the sectional angulation, are expressed mathematically as a function of $a_1$, $a_2$ and of the elements of triangle A by means of the following formulae:

$$(H - h) = \frac{2\,a1\,a2}{\sqrt{(a_1 - a_2)^2 + tg^2\,\theta\,(a_1 + A_2)^2}}$$

$$tg\left(\frac{\pi}{2} - \alpha\right) = tg^\theta \frac{a1 + a2}{a1 - a2}$$

It is then possible, by means of a small calculator, to program the calculation of h and $\alpha$ by feeding into the calculator the values $a_1$, $a_2$ and $\theta$; a computer may also be used for example a computer forming part of the tomodensitometric system, or else a pre-programmed function may be provided in the image visualization and analysis console.

It has already been pointed out that if it is desired to obtain completely the information defining any sectional plane, it was necessary to dispose triangles on each side of the part of the subject to be examined, and particularly of the head. It is to be noted that these two triangles may be disposed a little differently; for example a lateral triangle such as illustrated in FIGS. 6 and 7 and a frontal triangle may be used.

It is also possible, so as to increase the accuracy, particularly in sections situated towards the apexes of the triangles where the traces are smaller and so the measurements more difficult, to combine two triangles side by side; a first triangle having its apex juxtaposed to the basis of the second so as to form a parallelogram with its diagonal materialized.

If it is desired to obtain additional data for completely locating the position of the sectional planes in space, all that is required is to add to the two elements for locating the section in relation to an original plane $P_0$, a third locating element whose baseline is not parallel to those of the other two.

It is apparent that within the scope of the invention, modifications and different arrangements can be made other than are here disclosed. The present disclosure is merely illustrative with the ivention comprehending all variations thereof.

What is claimed as new and desired to be secured by Letters Patent of the United States is:

1. A method for using a tomodensitometer for making tomodensitometric images of tomodensitometric sections of a subject, said sections being spaced from one another in a first direction, said tomodensitometer including at least one elongated element having a longitudinal axis, said elongated element being formed at least partly from a material visible on said tomodensitometric sections, said elongated element comprising in cross section at least one characteristic having a magnitude varying substantially continuously along said longitudinal axis of said elongated element, said method comprising the steps of:

- using said at least one elongated element by disposing said at least one elongated element on said subject such that at least a portion of said longitudinal axis has a component which is disposed along a second direction perpendicular to the plane of each of said images; and
- using said tomodensitometer to form said images, whereby said elongated element forms a trace on each of said images, said trace having variations due to said at least one varying characteristic, and
- using said trace variations to accurately anatomically locate each of said sections.

2. The method as claimed in claim 1, wherein said step of using said at least one elongated element includes using at least one element further comprising a dimension perpendicular to said longitudinal axis and varying continuously along said longitudinal axis from one end of said longitudinal axis to another end of said longitudinal axis.

3. The method as claimed in claim 2, wherein said step of using said at least one elongated element includes using said at least one element further comprising an angular shape determined by first and second line segments having a common origin and forming therebetween an angle and a baseline.

4. The method as claimed in claim 3, wherein said step of using said at least one elongated element includes using said element having said baseline further comprising a reference baseline disposed perpendicular to the bisectrix of said angle.

5. The method as claimed in claim 4, wherein said step of using said at least one elongated element includes using at least one element further comprising a plurality of locating marks disposed thereon such that said marks are visible on said trace so as to enable accurate locating of sectional planes of said tomodensitometric sections sloping with respect to said baseline.

6. The method as claimed in claim 3, wherein said step of using said elongated element includes using at least one element further comprising triangular element having a constant density such that a trace of said at least one triangular element is visible in said tomodensitometric images and wherein said tomodensitometric sections are disposed parallel to said baseline such that the width of said trace provides a means for determining the distance of said tomodensitometric section from said baseline.

7. The method as claimed in claims 3 wherein said step of disposing said at least one elongated element includes the step of disposing first and second elements on said subject such that each said baseline of said first and second elements are parallel with respect to each other and are included within and define a reference plane for locating sectional planes of said tomodensitometric sections.

8. A device for providing accurate anatomical locating of tomodensitometric sections made on a subject by means of a tomodensitometer for making tomodensitometric images, said device comprising:

- at least one elongated element disposed on said subject in a reproducible way and being formed at least partly from a material visible on said tomodensitometric sections so as to form a trace therein and wherein said at least one element further comprises in cross section at least one characteristic having a magnitude varying substantially continuously along the great dimension of said at least one element,
- wherein said at least one element further comprises an element having a density substantially constant along the width of said at least one element and having a density varying substantially continuously along the length of said great dimension such that said locating is effected by measuring the radiological density of a trace of said at least one element in said tomodensitometric image.

9. A device for providing accurate anatomical locating of tomodensitometric sections made on a subject by means of a tomodensitometer for making tomodensitometric images, said device comprising:

- at least one elongated element disposed on said subject in a reproducible way and being formed at least partly from a material visible on said tomodensitometric sections so as to form a trace therein and wherein said at least one element further comprises in cross section at least one characteristic having a magnitude varying substantially continuously along the great dimension of said at least one element,
- wherein said at least one element further comprises a dimension perpendicular to said great dimension and varying continuously along said great dimension from one end of said great dimension to another end of said great dimension, said at least one element further comprising an angular shape determined by first and second line segments having a common origin and forming therebetween an angle and a base line, wherein said at least one element further comprises an element having a density substantially constant along the width of said at least one element and a density varying substantially continuously along the length of said great dimension such that said locating is effected by measuring the radiological density of said trace and the width of said trace in said tomodensitometric image.

10. A device for providing accurate anatomical locating of tomodensitometric sections made on a subject by means of a tomodensitometer for making tomodensitometric images, said device comprising:

- at least one elongated element disposed on said subject in a reproducible way and being formed at least partly from a material visible on said tomodensitometric sections so as to form a trace therein and wherein said at least one element further comprises in cross section at least one characteristic having a magnitude varying substantially continuously along the great dimension of said at least one element,
- wherein said at least one element further comprises a dimension perpendicular to said great dimension and varying continuously along said great dimension from one end of said great dimension to another end of said great dimension, said at least one element further comprising an angular shape determined by first and second line segments having a common origin and forming therebetween an angle and a base line, wherein said at least one element has a plurality of locating holes formed therein along said longitudinal axis at predetermined intervals such that said locating holes are visible along the width of said trace for improving the accuracy of said locating.

11. A device for providing accurate anatomical locating of tomodensitometric sections made on a subject by means of a tomodensitometer for making tomodensitometric images, said device comprising:

at least one elongated element disposed on said subject in a reproducible way and being formed at least partly from a material visible on said tomodensitometric sections so as to form a trace therein and wherein said at least one element further comprises in cross section at least one characteristic having a magnitude varying substantially continuously along the great dimension of said at least one element, wherein said at least one element further comprises a dimension perpendicular to said great dimension and varying continuously along said great dimension from one end of said great dimension to another end of said great dimension, said at least one element further comprising an angular shape determined by first and second line segments having a common origin and forming therebetween an angle and a base line, wherein said base line further comprises a reference base line disposed perpendicular to the bisectrix of said angle, wherein said at least one element further comprises a plurality of locating marks disposed thereon such that said marks are visible on said trace so as to enable accurate locating of sectional planes of said tomodensitometric sections sloping with respect to said base line, and wherein said locating marks further comprise at least one fine zone having a density different from that of said material forming said at least one element, and situated along said bisectrix.

12. Device as claimed in claim 11, wherein said fine zone further comprises a fine wire.

13. A device for providing accurate anatomical locating of tomodensitometric sections made on a subject by means of a tomodensitometer for making tomodensitometric images, said device comprising:

at least one elongated element disposed on said subject in a reproducible way and being formed at least partly from a material visible on said tomodensitometric sections so as to form a trace therein and wherein said at least one element further comprises in cross section at least one characteristic having a magnitude varying substantially continuously along the great dimension of said at least one element, wherein said at least one element further comprises a dimension perpendicular to said great dimension and varying continuously along said great dimension from one end of said great dimension to another end of said great dimension, said at least one element further comprising an angular shape determined by first and second line segments having a common origin and forming therebetween an angle and a base line, wherein said base line further comprises a reference base line disposed perpendicular to the bisectrix of said angle, wherein said at least one element further comprises a plurality of locating marks disposed thereon such that said marks are visible on said trace so as to enable accurate locating of sectional planes of said tomodensitometric sections sloping with respect to said base line, and wherein said at least one element further comprises a first and a second fine wire respectively coincident with said first and second line segments.

14. Means for providing accurate anatomical locating of tomodensitometric sections made on a subject by means of a tomodensitometer for making tomodensitometric images, said means comprising:

at least one elongated element disposed on said subject in a reproducible way and being formed at least partly from a material visible on said tomodensitometric sections so as to form a trace therein and wherein said at least one element further comprises in cross section at least one characteristic having a magnitude varying substantially continuously along the great dimension of said at least one element, wherein said at least one element further comprises a dimension perpendicular to said great dimension and varying continuously along said great dimension from one end of said great dimension to another end of said great dimension, said at least one element further comprising an angular shape determined by first and second line segments having a common origin and forming therebetween an angle and a base line, wherein said base line further comprises a reference base line disposed perpendicular to the bisectrix of said angle, and wherein said at least one element further comprises a plurality of locating marks disposed thereon such that said marks are visible on said trace so as to enable accurate locating of sectional planes of said tomodensitometric sections sloping with respect to said base line, said means further comprising a plotter having a shape identical to said angular shape of said at least one element.

15. Means as claimed in claim 14 wherein said plotter further comprises a chart including a circular angle protractor.

16. Means as claimed in claim 14 wherein said at least one element further comprises first and second elements disposed on a part of said subject to be examined such that said baseline of each of said first and second elements are parallel with respect to each other and are located within and define a reference plane for locating sectional planes of said tomodensitometric sections disposed at any angle with respect to said reference plane.

17. In a tomodensitometer for making tomodensitomeric images of tomodensitometric sections spaced from one another in a first direction, means disposed on a subject for providing accurate anatomical locating of said tomodensitometric sections, said means comprising at least one elongated element having a longitudinal axis, at least a portion of which has a component which is disposed along a second direction perpendicular to the plane of said images, said elongated element being formed at least partly from a material visible on said tomodensitometric sections so as to form a trace therein and wherein said at least one element further comprises in cross section at least one characteristic having a magnitude varying substantially continuously along said longitudinal axis of said at least one element;

wherein said at least one element further comprises an angular shape determined by first and second line segments having a common origin and forming therebetween an angle and a baseline;

wherein said at least one element further comprises first and second elements disposed on said subject such that each said baseline of said first and second elements are parallel with respect to each other and are included within and define a reference plane for locating sectional planes of said tomodensitometric sections;

further comprising a hoop member wherein said first and second elements are fixed on said hoop member and said hoop member is disposed about a part of said subject to be examined.

18. Means as claimed in claim 17 wherein said first and second elements are fixed with respect to each other symmetrically on said hoop.

19. Means as claimed in claim 18 wherein said part of said subject to be examined further comprises a head having first and second auditory apertures and wherein said hoop further comprises first and second adapters for introduction into said auditory apertures of said subject such that a central portion of said hoop is disposed on a nasion of said subject and said hoop is disposed in the orbito-meatal plane of said subject.

* * * * *